United States Patent [19]

Oyama et al.

[11] Patent Number: 4,536,342
[45] Date of Patent: Aug. 20, 1985

[54] PROCESS FOR PRODUCING A HALOGEN-CONTAINING ETHYLBENZENE DERIVATIVE

[75] Inventors: Kiyotaka Oyama, Hikari; Tuneo Harada, Shin-nanyo, both of Japan

[73] Assignee: Toyo Soda Manufacturing Co., Ltd., Shin-nanyo, Japan

[21] Appl. No.: 658,047

[22] Filed: Oct. 5, 1984

[30] Foreign Application Priority Data

Oct. 5, 1983 [JP] Japan .................................. 58-185023

[51] Int. Cl.$^3$ ..................... C07C 121/66; C07C 69/76; C07C 53/134
[52] U.S. Cl. ................. 260/465 G; 560/105; 562/496; 564/182
[58] Field of Search .................. 260/465 G; 560/105; 562/496; 564/182

[56] References Cited

U.S. PATENT DOCUMENTS 4,145,362  3/1979  Brepoels et al. ................ 260/465 G

OTHER PUBLICATIONS

Brunner et al., Chemical Abstracts, vol. 44, 1054, (1950).
Kost et al., Chemical Abstracts, vol. 47, 2759, (1953).
Dombrovskii et al., Chemical Abstracts, vol. 51, 8038, (1957).
Dombrovskii et al., Chemical Abstracts, vol. 52, 9019, (1958).
Rondestvedt, Jr., Organic Reactions, vol. 24, pp. 225-259, (1976).

*Primary Examiner*—Dolph H. Torrence
*Attorney, Agent, or Firm*—Oblon, Fisher, Spivak, McClelland & Maier

[57] ABSTRACT

A process for producing a halogen-containing ethylbenzene derivative represented by the general formula:

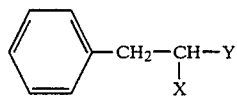

(I)

where X is a halogen atom, and Y is a nitrile group, a carboxyl group, a lower alkoxycarbonyl group or an amidocarbonyl group, which comprises reacting a vinyl compound represented by the general formula:

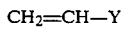

(II)

where Y is as defined above, with a benzenediazonium salt and halogen ions in a solvent mixture comprising a lower alcohol and/or an ether, and water, under an acidic condition with a mineral acid, in the presence of a monovalent copper compound as a catalyst.

5 Claims, No Drawings

PROCESS FOR PRODUCING A HALOGEN-CONTAINING ETHYLBENZENE DERIVATIVE

The present invention relates to a process for producing a halogen-containing ethylbenzene derivative. More particularly, the present invention relates to a process for producing a halogen-containing ethylbenzene derivative, which comprises reacting a vinyl compound with a benzenediazonium salt and halogen ions in the presence of a catalyst.

Halogen-containing ethylbenzene derivatives such as α-halogeno-β-phenyl-substituted propionitriles, α-halogeno-β-phenyl-substituted propionic acids and their esters and amides, are useful substances, which can be converted to phenylalanine i.e. an important amino acid, by amination and, if necessary, hydrolysis. These halogen-containing ethylbenzene derivatives may be prepared by reacting a vinyl compound such as acrylonitrile, acrylic acid, an acrylate or an amide with a benzenediazonium salt and halogen ions.

Heretofore, in this method (i.e. a method using a so-called Meerwein reaction), it has been most common to conduct the reaction by using a copper compound catalyst in a solvent mixture comprising acetone and an aqueous hydrochloric acid solution and by adding sodium acetate (W.H. Brunner et at., Chemical Abstract, vol. 44, 1054h (1950); A. N. Kost et al., Chemical Abstract, vol. 47, 2759i (1953); A. V. Dombrovskii, Chemical Abstract, vol. 51, 8038f (1957), and ibid., vol. 52, 9019i (1958)). However, from the industrial point of view, this process has a problem in that it requires a great amount of sodium acetate. On the other hand, R. Filler et al. have reported on a process for conducting the reaction in a solvent mixture comprising acetone and an aqueous hydrochloric acid solution without using sodium acetate. However, in this process, the yield is not high enough (Proc. Chem. Soc., 117 (1962) and Can. J. Chem., vol. 45, 329 (1967)). Further, in these processes, from the nature of the reaction mechanism, it is impossible to avoid the side reaction whereby a part of acetone as the solvent is converted into chloroacetone (C.S. Rondestvedt Jr., Org. Reaction, vol. 11, 189 and vol. 24, 225).

Acetonitrile, N-methylpyrrolidone, dimethylsufoxide, sulforan and dimethylsulforan have been regarded as fairly satisfactory solvents in certain cases. However, alcohols and ethers having a mere unshared electron pair have been believed to be incapable of satisfying the required functions (C. S. Rondestvedt Jr., Org. Reaction, vol. 11, 189).

The present inventors have conducted extensive researches on processes for preparing halogen-containing ethylbenzene derivatives, particularly β-phenylsubstituted α-halogenopropionitriles and α-halogenopropionic acids and their esters and amides, by means of the Meerwein reaction, and unexpectedly found that alcohols and ethers which have been regarded as being unsuitable as a solvent for this reaction, are capable of forming an excellent solvent system under a certain condition, particularly under a condition where the vinyl compound is used in an adequate excess amount. The present invention has been accomplished based on this discovery.

Namely, the present invention provides a process for producing a halogen-containing ethylbenzene derivative represented by the general formula:

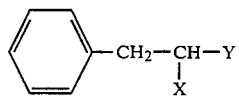 (I)

where X is a halogen atom, and Y is a nitrile group, a carboxyl group, a lower alkoxycarbonyl group or an amidocarbonyl group, which comprises reacting a vinyl compound represented by the general formula:

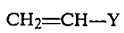 (II)

where Y is as defined above, with a benzenediazonium salt and halogen ions in a solvent mixture comprising a lower alcohol and/or an ether, and water, under an acidic condition with a mineral acid, in the presence of a monovalent copper compound as a catalyst.

Now, the present invention will be described in detail with reference to the preferred embodiments.

The vinyl compound used as the starting material in the process of the present invention includes acrylonitrile, acrylic acid, its lower alkyl esters and amides. In the case where a lower alkyl ester of acrylic acid is used as the starting material (i.e. in the case where an α-halogeno-β-phenylpropionate is produced), the lower alkoxy moiety, i.e. the lower alkoxy moiety in the case where Y in both of the general formulas is a lower alkoxycarbonyl group, may be a methoxy group, an ethoxy group, a propoxy group or butoxy group.

The benzenediazonium salt used as the other starting material in the process of the present invention, may be used in the state of the acidic solution obtained by reacting aniline with nitrous acid or a nitrite under an acidic condition by a conventional method. The aqueous acidic solution of the benzenediazonium salt thus prepared can be used as it is and it is unnecessary to adjust the pH by partially neutralizing the solution. However, so long as the acidic condition is maintained, the solution may partially be neutralized with a weak alkaline substance such as sodium acetate, sodium hydrogen carbonate or sodium carbonate, if desired.

In the process of the present invention, the amount of the vinyl compound relative to the benzenediazonium salt is very important. It is necessary that the amount of the vinyl compound is at least the stoichiometric amount relative to the benzenediazonium salt. It is usual that the vinyl compound is used in an amount of from about 1 to about 7 mols, preferably from about 1.5 to about 5 mols, relative to 1 mol of the benzenediazonium salt.

As the lower alcohol used for the solvent mixture with water in the process of the present invention, there may be mentioned an aliphatic lower alcohol such as methanol, ethanol, propanol or butanol, and a polyol such as ethylene glycol, propylene glycol or glycerin. As the ether, there may be mentioned ethers having good affinity with water, such as tetrahydrofuran, 1,4-dioxane, and a mono- and di-alkyl ether (the alkyl group may be a methyl group or an ethyl group) of ethylene glycol. These alcohols or ethers, may be used in combination as a mixture of two or more different kinds.

These lower alcohols and/or ethers are employed in an amount of from about 0.1 to about 3 liters, preferably from about 0.15 to about 1.5 liters, most preferably from 0.2 to 1 liter, relative to 1 mol of the benzenediazonium salt as the starting material, in combination with water.

The amount of the water calculated as an aqueous mineral acid solution inclusive of the mineral acid to impart acidity to water, is likewise usually from about 0.1 to about 1 liter, preferably from about 0.15 to about 0.7 liter, most preferably from 0.2 to 0.5 liter, relative to 1 mol of the benzenediazonium salt as the starting material.

The process of the present invention is conducted under an acidic condition with a mineral acid. As the mineral acid imparting such an acidic condition, there may be mentioned a hydrohalogenic acid such as hydrochloric acid or hydrobromic acid, an oxygen acid such as sulfuric acid, nitric acid, phosphoric acid or perchloric acid, or a mixture thereof. The amount of the acid is not critical so long as it is able to maintain the reaction system under an acidic condition. However, the reaction may be conducted under a relatively strong acidic condition, e.g. at a pH of 1 or less, which is not usually employed for the Meerwein reaction.

It is common to use an excess amount of an acid for the preparation of a benzenediazonium salt by the reaction of aniline with a nitrite, and accordingly, the excess amount may be utilized for this purpose.

According to the process of the present invention, the above-mentioned two starting materials are reacted with halogen ions. As the halogen ions, there may be mentioned chlorine ions, bromine ions and iodine ions. The amount of the halogen ions is at least the stoichiometric amount relative to the benzenediazonium ions in the starting materials. When a hydrohalogenic acid is used for the preparation of the benzenediazonium salt as the starting material, this condition is satisfied without any further addition of halogen ions. However, when halogen ions are not adequately contained in the starting materials, it is necessary to add a salt containing halogen ions or a hydrohalogenic acid for the reaction. In the process of the present invention, the halogen ions may be present in great excess.

In the process of the present invention, a monovalent copper compound is used as a catalyst. As such a compound, there may be mentioned cuprous oxide, cuprous chloride, cuprous bromide, cuprous iodide or cuprous cyanide. Such a copper compound may be added to the reaction system in the form of a powder, or it may be employed as dissolved in a proper solvent. The amount of the copper compound is not critical. However, it is common to use it in an amount of at least about 0.01 mol and usually at most about 1 mol, relative to 1 mol of the benzenediazonium salt as the starting material. When it is used in a great amount, it is necessary to take due care not to permit an abnormal temperature rise of the reaction system, as mentioned hereinafter.

The reaction of the benzenediazonium salt with the vinyl compound proceeds exothermally when the copper compound catalyst is added. Therefore, in order to avoid side reactions such as the decomposition of the benzenediazonium salt or the polymerization of the vinyl compound, it is preferred to conduct the process of the present invention under cooling, usually at a temperature within a range of from about −30° to about 50° C., preferably from about −10° to about 40° C., more preferably from about 0° to about 30° C. Further, it is preferred that the catalyst (particularly when used in a relatively large amount) is added portionwise or continuously gradually to the reaction system so as to maintain the temperature within the above-mentioned range.

After the completion of the reaction, the formed halogen-containing ethylbenzene derivative can be isolated by a conventional operation such as extraction or distillation.

In the process of the present invention, it is unnecessary to control the pH of the reaction system by using a buffering agent such as sodium acetate, and the reaction is conducted under an acidic condition with a mineral acid, whereby a side reaction such as a diazocoupling reaction, formation of a phenol due to the decomposition of the benzenediazonium salt, or the formation of halogenated benzenes by the Sandmeyer reaction, are minimum. Furthermore, there is no side reaction for the formation of a halide of the solvent. Thus, according to the present invention, the desired halogen-containing ethylbenzene derivative can be produced in good yield.

Now, the present invention will be described in further detail with reference to Examples. However, it should be understood that the present invention is by no means restricted to these specific Examples.

EXAMPLE 1

55.8 g (0.6 mol) of aniline and 200 ml of a 25% hydrochloric acid aqueous solution were mixed to obtain a suspension of aniline hydrochloride. While cooling this solution to a temperature of from 0° to 10° C. from outside and stirring it, a solution prepared by dissolving 42.5 g (0.615 mol) of sodium nitrite in 85 ml of distilled water, was dropwise added over a period of about 4 hours. After the completion of the dropwise addition, the reaction mixture was stirred for about 1 hour at a temperature of from 0° to 10° C. To this solution, 200 ml of methanol and 95.4 g (1.8 mols) of acrylonitrile were added, and while stirring the mixture under cooling, 5 g of cuprous oxide powder was gradually added. The reaction mixture was stirred at a temperature of from 10° to 20° C. for 4 hours, and then methanol and unreacted acrylonitrile were distilled off by distillation. The residual solution was separated into an aqueous phase and an organic phase. The organic phase was subjected to distillation under reduced pressure, whereby 87 g (yield: 88%) of α-chloro-β-phenylpropionitrile was obtained. (b.p.: 105°–110° C./4 mmHg).

EXAMPLES 2 to 4

The reactions were conducted in the same manner as in Example 1 except that various solvents were used instead of methanol. The yields of α-chloro-β-phenylpropionitrile as determined by gas chromatography are shown in Table 1.

TABLE 1

| Example No. | Solvent (amount) | Yield (%) |
|---|---|---|
| 2 | Ethanol (400) | 88 |
| 3 | Isopropanol (200) | 86 |
| 4 | Tetrahydrofuran (200) | 83 |

EXAMPLE 5

The reaction was conducted in the same manner as in Example 1 except that cuprous chloride was used instead of cuprous oxide. The yield of α-chloro-β-phenylpropionitrile determined by gas chromatography was 86%.

EXAMPLE 6

The diazotization reaction was conducted in the same manner as in Example 1 except that 300 ml of 40% sulfuric acid was used instead of 200 ml of the 25% hydrochloric acid aqueous solution in Example 1. After the completion of the diazotization reaction, 40 g of sodium chloride, 31.8 g of acrylonitrile and 400 ml of methanol were added and mixed with the reaction mixture. Then, while stirring the mixture under cooling with ice, a solution prepared by dissolving 5 g of cuprous oxide in 25 ml of concentrated hydrochloric acid, was dropwise added. The stirring was continued at a temperature of from 10° to 20° C. for about 4 hours, and then the after-treatment was conducted in the same manner as in Example 1, whereby α-chloro-β-phenyl-propionitrile (yield: 72% as measured by gas chromatography) was obtained.

EXAMPLES 7 to 9

The reactions were conducted in the same manner as in Example 1 except that methyl acrylate, acrylamide and acrylic acid were, respectively, used instead of acrylonitrile in Example 1. The results are shown in Table 2.

TABLE 2

| Example No. | Vinyl Compound (amount, g) | Product | Yield (%) | Analytical method |
|---|---|---|---|---|
| 7 | Methyl acrylate (155) | Methyl α-chloro-β-phenylpropionate | 59 | Gas chromatography |
| 8 | Acrylic acid amide (128) | α-chloro-β-phenyl-propionic acid amide | 60 | Gas chromatography |
| 9 | Acrylic acid (130) | α-chloro-β-phenyl-propionic acid | 51 | Liquid chromatography |

EXAMPLE 10

The reaction was conducted in the same manner as in Example 1 except that 300 ml of a 30% hydrobromic acid aqueous solution and 400 ml of methanol were used instead of the 25% hydrochloric acid aqueous solution. After the completion of the reaction, the after-treatment was conducted in the same manner as in Example 1, and α-bromo-β-phenylpropionitrile was obtained by the distillation under reduced pressure in a yield of 75% (b.p.: 87°–88° C/0.2 mmHg).

We claim:

1. A process for producing a halogen-containing ethylbenzene derivative represented by the general formula:

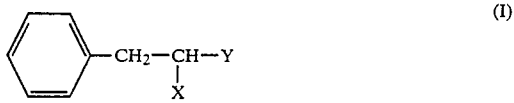

(I)

where X is a halogen atom, and Y is a nitrile group, a carboxyl group, a lower alkoxycarbonyl group or an amidocarbonyl group, which comprises reacting a vinyl compound represented by the general formula:

(II)

where Y is as defined above, with a benzenediazonium salt and halogen ions in a solvent mixture comprising a lower alcohol and/or an ether, and water, under an acidic condition with a mineral acid, in the presence of a monovalent copper compound as a catalyst.

2. The process according to claim 1, wherein the vinyl compound is used in great excess relative to the benzenediazonium salt.

3. The process according to claim 1, wherein the mineral acid is a hydrohalogenic acid, sulfuric acid, nitric acid, phosphoric acid or perchloric acid.

4. The process according to claim 1, wherein the halogen ions are chlorine, bromine or iodine ions.

5. The process according to claim 1, wherein the monovalent copper compound is cuprous oxide, cuprous chloride, cuprous bromide, cuprous iodide or cuprous cyanide.

* * * * *